(12) United States Patent
Ford Morie et al.

(10) Patent No.: US 7,484,716 B2
(45) Date of Patent: Feb. 3, 2009

(54) SCENT DELIVERY DEVICE AND METHOD OF SIMULATING SCENT IN A VIRTUAL ENVIRONMENT

(75) Inventors: Jacquelyn Ford Morie, Los Angeles, CA (US); Donat-Pierre Luigi, Santa Monica, CA (US); Corinna Lathan, Wheaton, MD (US); Matthew Pettersen, Berwyn Heights, MD (US); Jack Maxwell Vice, Washington, DC (US)

(73) Assignee: University of Southern California, Los Angeles, CA (US)

( * ) Notice: Subject to any disclaimer, the term of this patent is extended or adjusted under 35 U.S.C. 154(b) by 317 days.

(21) Appl. No.: 11/107,493

(22) Filed: Apr. 14, 2005

(65) Prior Publication Data

US 2006/0065986 A1 Mar. 30, 2006

Related U.S. Application Data

(60) Provisional application No. 60/562,505, filed on Apr. 14, 2004.

(51) Int. Cl.
*B01F 3/04* (2006.01)

(52) U.S. Cl. .................. 261/26; 261/30; 261/DIG. 88; 422/124; 239/58; 239/59

(58) Field of Classification Search .................. 261/26, 261/30, DIG. 88; 55/467; 422/124; 239/58, 239/59
See application file for complete search history.

(56) References Cited

U.S. PATENT DOCUMENTS

| | | | |
|---|---|---|---|
| 5,591,409 A | 1/1997 | Watkins | |
| 5,724,256 A | 3/1998 | Lee et al. | |
| 6,406,004 B1 * | 6/2002 | Ude | 261/26 |
| 6,494,778 B2 | 12/2002 | Kossak et al. | |
| 6,803,987 B2 * | 10/2004 | Manne | 352/85 |

OTHER PUBLICATIONS

International Search report dated Sep. 5, 2006 from corresponding PCT application lists references above.

* cited by examiner

*Primary Examiner*—Robert A Hopkins
(74) *Attorney, Agent, or Firm*—Hogan & Hartson LLP (57) ABSTRACT

A cartridge for releasing scents through a digital trigger mechanism. Also disclosed is a portable, wearable, lightweight necklace or "collar," capable of holding 1 to 12 cartridges.

6 Claims, 6 Drawing Sheets

SCENT DELIVERY DEVICE AND METHOD OF SIMULATING SCENT IN A VIRTUAL ENVIRONMENT

CROSS-REFERENCE TO PRIOR APPLICATION

This application claims the benefit of prior U.S. Provisional Application No. 60/562,505 filed Apr. 14, 2004, which application is hereby incorporated by reference.

This invention was made with support in part by a grant from U.S. Army Research Office (DAAD19-99-D-0046). Therefore, the U.S. government has certain rights.

FIELD OF THE INVENTION

The present invention relates to olfactory stimulation. More specifically, the invention relates to scent delivery devices, methods and applications.

BACKGROUND OF THE INVENTION

Smell is a sensory modality that can generate strong emotions but is rarely used within virtual training environments. As the most evocative of our senses, smell can be used to contrast or heighten particular emotional effects, and provide an increased sense of richness or fidelity to a virtual scene. Our sense of smell differs from sight and sound in two important ways. First of all, we smell by means of an actual intake of molecules with which our body interacts. Thus it is a chemical sense (as is taste). Secondly, smell is first processed by the emotional parts of the brain, and is rationally analyzed only after some delay (Pine, 1995, Howard Hughes Medical Institute Report, pp. 48-55). Both these aspects have implications for smell's use within training environments.

However, smell is probably the least explored and understood design challenge in a virtual environment, although it promises much in regard to its power to augment emotional experience, including emotional experiences in virtual environments. As such, there is an ongoing need for scent delivery devices that can be used to enhance emotional experiences, especially emotional experiences in virtual environments.

SUMMARY OF THE INVENTION

It is one object of the present invention to formulate a new design for virtual environments that utilizes multiple sensory inputs to induce a feeling of presence within the virtual environment. Deviating from virtual reality's twenty-year focus on photo-realism, this "feels-real" design alternative aims directly at understanding the interdependencies of sensory stimuli in their creation of mental constructs, and the subsequent degree of realism perceived.

It is another object of the present invention to provide a portable, wearable, scent delivery device capable of providing 1-12 distinct scents in a single simulation.

It is another object of the present invention to provide a reuseable, refillable or replaceable scent delivery system for use in multiple simulations.

It is another object of the present invention to provide a scent delivery device having tunable intensity control to vary the amount of scent released.

It is another object of the present invention to provide a scent delivery device capable of rapid dissipation of the scent released and minimum sound generation.

It is another object of the present invention to provide a scent delivery system with a digital trigger mechanism to deploy individual scents from simulation control, including wireless trigger.

The present invention relates to devices and methods for creating olfactory perception for a person in a virtual reality environment by introducing scents in synchronism with visual and/or acoustic representations. Alternatively, such smells can be deployed with this device in a real environment for various medical, training, or entertainment purposes. The scents are supplied to the person either in mixed groups or separately as individual scents.

Accordingly, in one aspect, the invention features a scent cartridge, comprising: a scent reservoir having a basin, a lid and a scented material placed in the basin, wherein the lid has scent passages; a housing fixably connected to the scent reservoir and defining an enclosure with an opening; a valve fixably connected to the lid of the scent reservoir, the valve covering variably a portion of the scent passages; a fan connected to the housing and positioned at least partially inside the housing such that, when operating, the fan directs air from within the housing to the outside of the housing, through the opening; means for varying the portion of the scent passages covered by the valve; and means for varying the rotation speed of the fan. The means for varying the portion of the scent passages covered by the valve may include a motor connected to a computer via a motor controller, and the position of the valve is controlled according to a signal received from the computer. The means for varying the speed of the fan may include a motor and is electrically connected to a speed control circuit. The speed control circuit and the motor are each connected to a computer via a motor controller, and the rotational speed of the fan is controlled by a signal received from the computer. Preferably, the cartridge is wearable.

In another aspect, the invention features a scent delivery cartridge, comprising: a scent reservoir having a basin, a lid and a scented material placed in the basin, wherein the lid has scent passages; a housing fixably connected to the scent reservoir and defining an enclosure with an opening; a valve fixably connected to the lid of the scent reservoir and variably covering a portion of the scent passages, wherein the valve is connected to a motor which is connected to a computer via a first motor controller, and wherein the position of the valve is controlled by a signal received from the computer; and a fan connected to the housing and positioned at least partially inside the housing such that, when operating, the fan directs air from within the housing to the outside of the housing, through the opening, wherein the fan is electronically connected to a motor and a speed control circuit, and the speed control circuit and the motor are each connected to a computer via a second motor controller, and wherein the rotational speed of the fan is controlled by a signal received from the computer. Preferably, the cartridge is wearable.

The scent cartridge of the invention may be used in a scent delivery system which is preferably wearable. In one embodiment, the scent delivery system comprises a base adapted for holding at least one or more scent cartridges; one or more scent cartridges detachably fixed to the base, each one or more scent cartridges having a scent reservoir and a valve, wherein the scent reservoir includes a basin, a scented material placed in the basin, and a lid containing scent passages, and wherein the valve is fixably connected to the lid of the scent reservoir and variably covers a portion of the scent passages; a communication board detachably fixed to the base, containing a controller and a microprocessor, wherein the microprocessor is capable of receiving input signals from a signal generator (e.g., a computer) through an electronic connection (e.g., a wireless connection), processing the input signals, and transmitting output signals through the controller to the valve for scent release; and a power supply detachably fixed to the base, providing power to the scent cartridges and the communication board.

In another embodiment of the scent delivery system, the scent cartridge further comprises a housing fixably connected to the scent reservoir and defining an enclosure with an opening; and a fan connected to the housing and positioned at least partially inside the housing, wherein the microprocessor is further capable of transmitting output signals through the controller to the fan for directing scented air from within the housing to the outside of the housing through the opening.

The scent delivery system of the invention can be used for controlled scent release. In particular, it can be combined with audio and video components to create a multimedia virtual reality environment.

Accordingly, the invention provides a method for scent release, comprising providing a wearable scent delivery system (e.g., as described above) comprising one or more scent cartridges, each cartridge containing a different scent; and releasing one or more scents from one or more cartridges in a pre-determined order for a pre-determined duration at a pre-determined intensity.

The invention also provides a method of simulating the olfactory component of a virtual reality environment. The method involves providing a visual and acoustic representation; providing a wearable scent delivery system (e.g., as described above) comprising one or more scent cartridges, each cartridge containing a different scent; and releasing one or more scents from one or more cartridges in a pre-determined order for a pre-determined duration at a pre-determined intensity in synchronism with the visual and acoustic representation.

Research proves that the olfactory sense is nearly 10,000 times as sensitive as taste, and is actually the main source for the flavors of food. There is also strong adaptation, where one soon becomes accustomed to an odor and unaware of it, as well as masking of one odor by another, the theory of perfume. Due to the power of the olfactory sense, there are many other uses that can be developed for a controlled wearable scent delivery device. For example, it can be used for training of soldiers, as a memory aid, for entertainment, other forms of education, or as a comfort device for children with mental or physical challenges.

The above-mentioned and other features of this invention and the manner of obtaining and using them will become more apparent, and will be best understood, by reference to the following description, taken in conjunction with the accompanying drawings. These drawings depict only typical embodiments of the invention and do not therefore limit its scope.

DETAILED DESCRIPTION OF THE INVENTION

The present invention is generally directed to a wearable scent delivery device meant to enhance the virtual reality environment, and more specifically to a lightweight scent delivery device that that can be comfortably worn by a person in a virtual reality environment.

As shown in FIG. 1, the scent delivery device 1 includes a base 10 adapted for holding scent cartridges and a series of scent cartridges 50 containing one or more different scents (not shown) required for a given scenario. The base 10 must be adapted to hold at least one scent cartridge, and preferably it is adapted to hold a plurality of scent cartridges. Most preferably, the base is adapted to be capable of holding 10-12 scent cartridges.

Figure 1A:
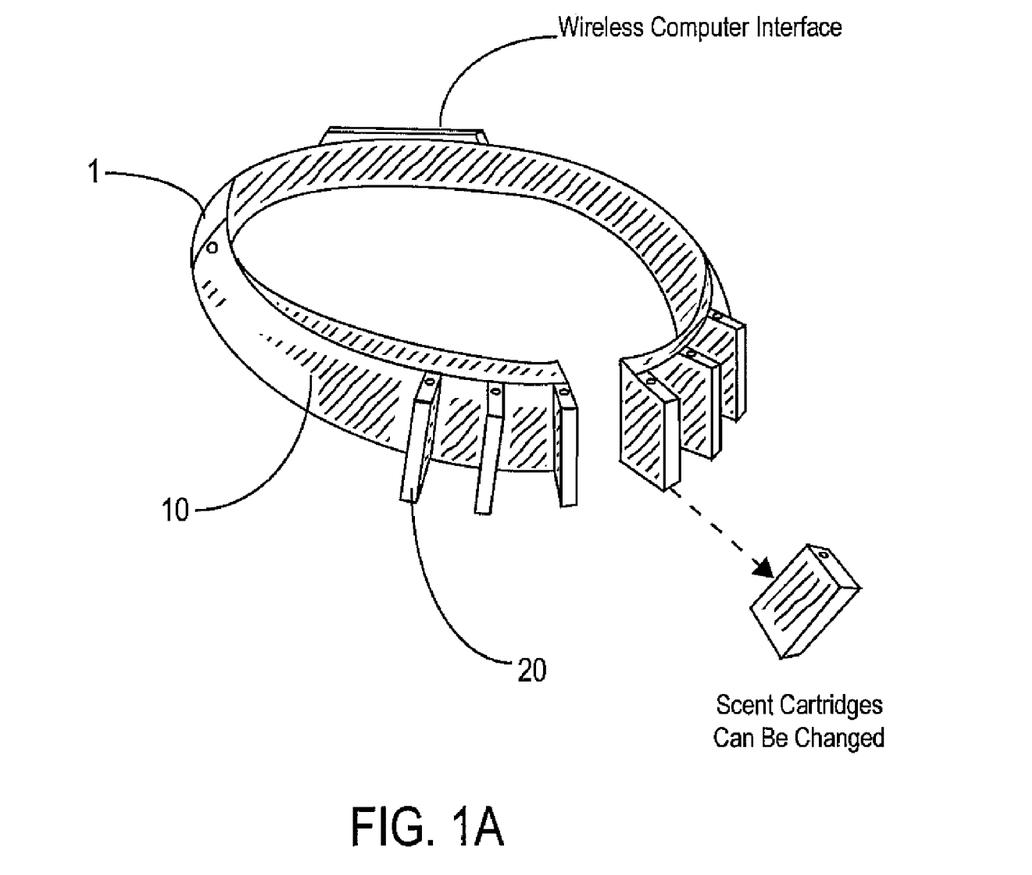
FIG. 1 illustrates the scent delivery device according to the present invention.
Figure 1B:
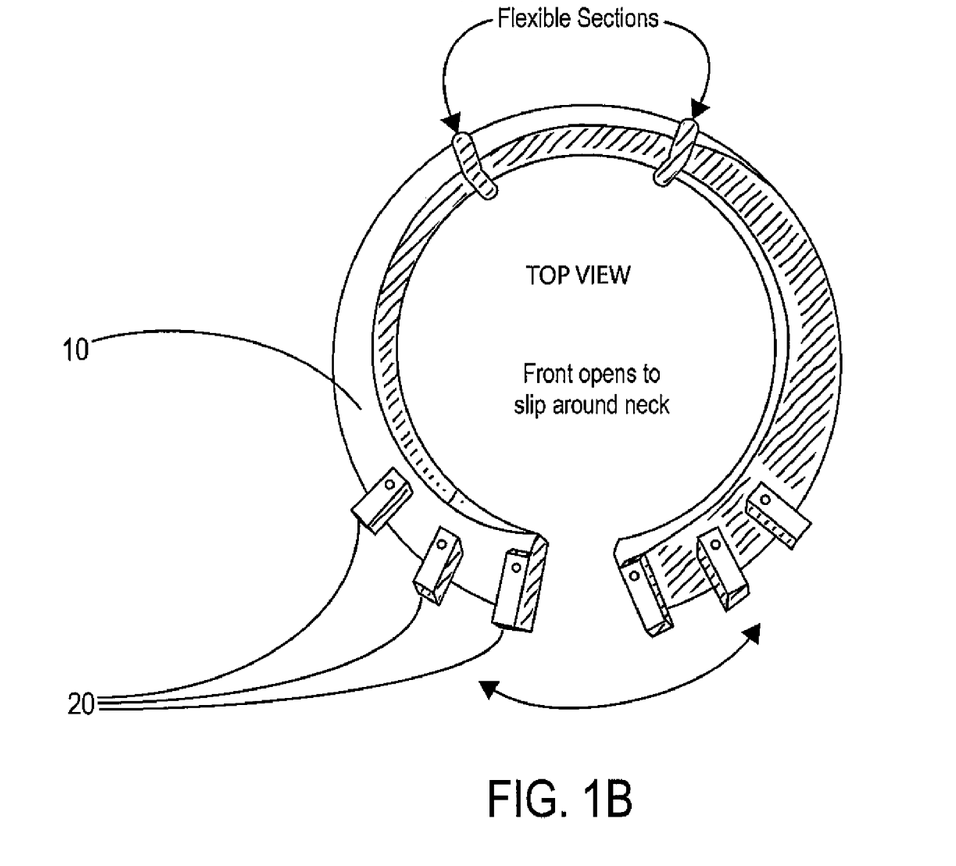

As shown in FIG. 1B, the scent cartridges 50 are detachably connected to the base 10 so that the cartridges are easily interchangeable in order to allow a different combination of scents to be chosen from a scent library for various virtual reality environments. The manner in which the scent cartridges are detachably mountable on the base is not particularly limited, and may include such means as a screw, a slot, a clip, a hook, or a pressure-locked fitting within the base. Preferably, the cartridges can be easily swapped on and off of the base to quickly change the scents. Most preferably, the cartridges can be swapped on and off of the base with no tools and in a few seconds. Preferably, the scent cartridges 50 are reuseable and refillable.

Figure 1C:
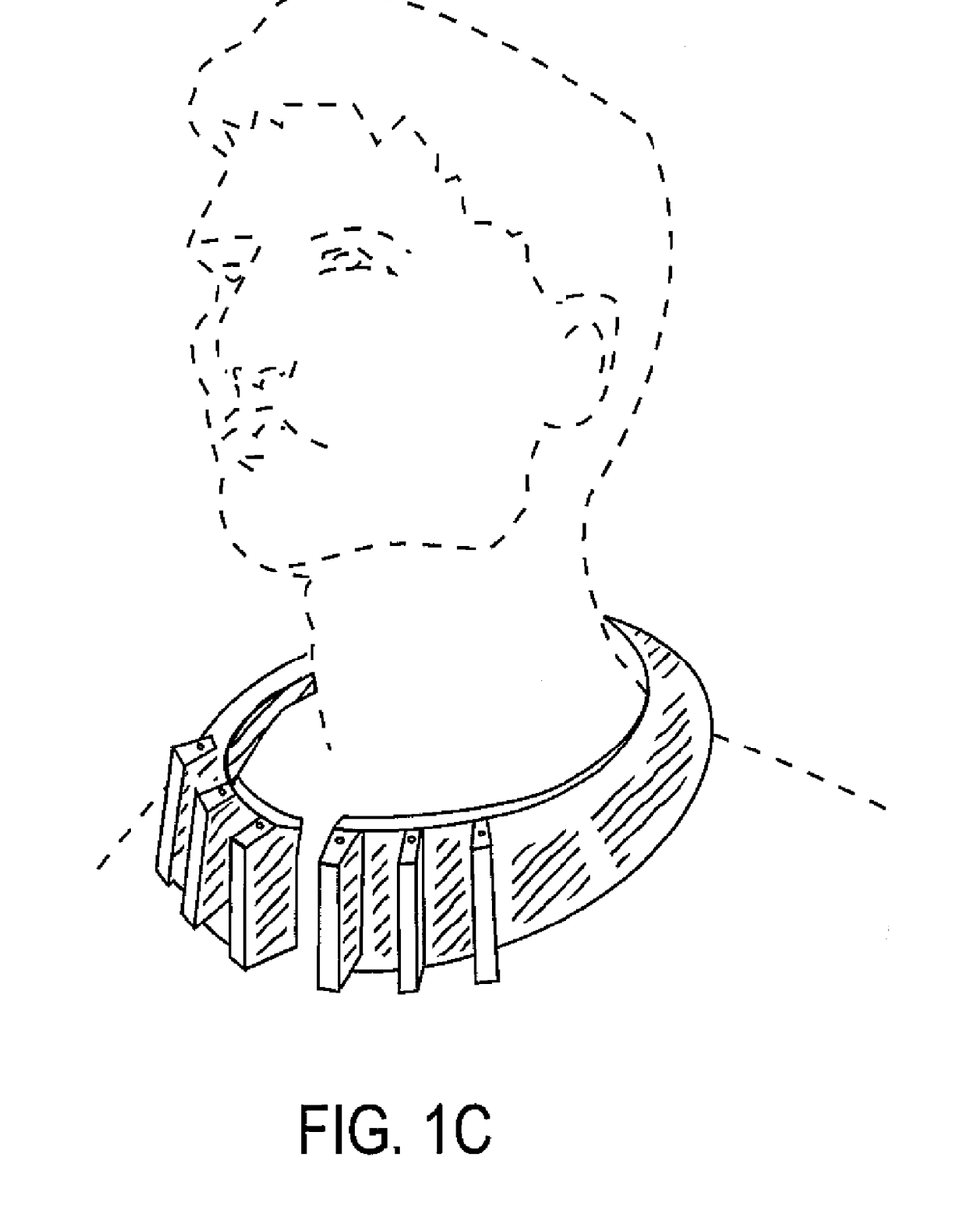

The base 10 is not limited to a particular shape so long as it is portable and wearable. As shown in FIGS. 1A-1C, the base 10 may be in the shape of a "collar" or "necklace." However, it is not required that the base 10 should be in the shape of a collar or necklace. Other shapes or items that are portable and wearable including a lightweight backpack, a belt, an armband or a bracelet may be used. In the specification, when the term "collar" or "necklace" is used, it may be used interchangeably with the term "scent delivery device" and its use should not be interpreted as limiting the invention to the shape or appearance of a collar or necklace unless explicitly stated.

Preferably, the cartridges 50 are computer controlled in response to the virtual reality environment, and include a digital trigger mechanism to deploy individual scents from simulation control, including wireless trigger.

Figure 2:
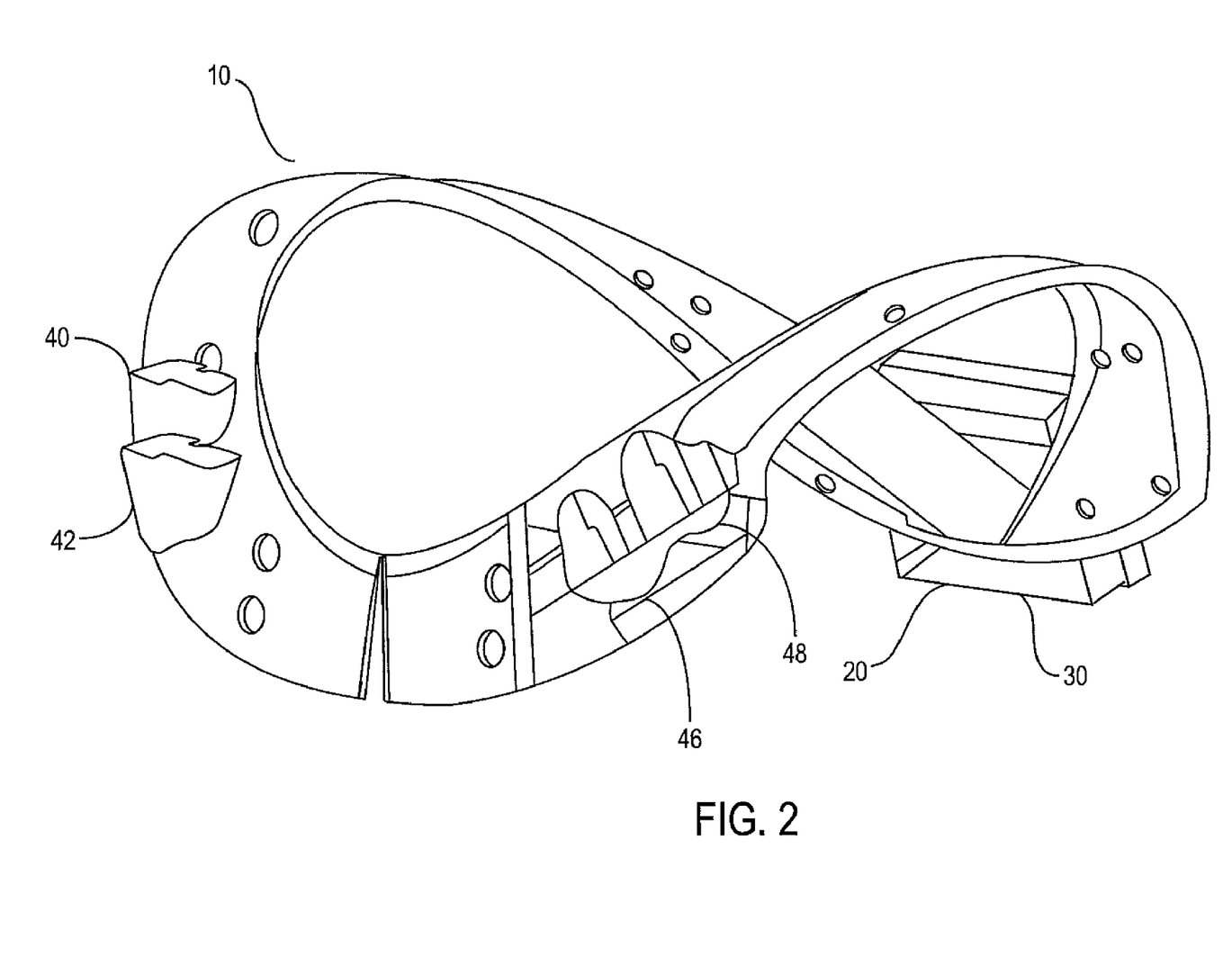
FIG. 2 illustrates an embodiment of the base for the scent delivery device according to the present invention.

An exemplary base 10 for the scent delivery system according to the present invention is illustrated in FIG. 2. The base 10 is in the form of a necklace and includes cartridge slots 40, 42, 46, and 48. Scent cartridges are fitted into the cartridge slots by a screw or other securing mechanism. Preferably, the base includes a communication board 20. Preferably, the base includes a battery 30 for powering the various electrical components of the base and the scent cartridges. Preferably, the batteries, communication board and cartridges are all connected with wires, circuit board, or conducting polymer. Alternatively, they can be connected through use of smart fabrics that are woven with integrated wires within the fibers.

Preferably, the base can be manufactured or molded of various lightweight materials, including but not limited to: various plastics, resin, epoxy, composite materials, carbon fiber, or metals such as titanium, molybdenum, or aluminum.

Preferably, the exemplary cartridges are fixably connected to the base 10 by being placed into a custom fitted slot and secured with pressure, or a securing device such as a small screw, hook, or clip.

The device is powered by small batteries such as disposable or rechargeable commercially available batteries such as alkaline, Nickel-Cadmium, Nickel Metal Hydride, alkaline manganese with or without memory. The exemplary device uses 9V and 1.5V AA size batteries. Preferably the battery portion of the device is fixably connected to the base within a small case or compartment built into or affixed to the main body of the base, with the compartment having a cover securing the batteries within the case, fixably connected to the base and the battery housing by means of a screw, clip, hook or snap. Alternatively, the batteries can be contained in a small pack that is separate from the base but connected to the controller in the base by means of the required electrical wires.

Preferably, the communication board is integrated into a space within the base and secured with pressure, clips, a slot, or a small screw. Preferably, the communications board comprises a controller for fan speed and valve position; a microprocessor, and preferably a wireless connection to the computer. Alternatively, the connection to the computer can comprise a wired connection such as a serial or parallel cable.

Preferably the communication board receives bytes of data through the wireless or wired connection which are translated into voltage variation signals regulating the valve position and fan speed.

Figure 3:
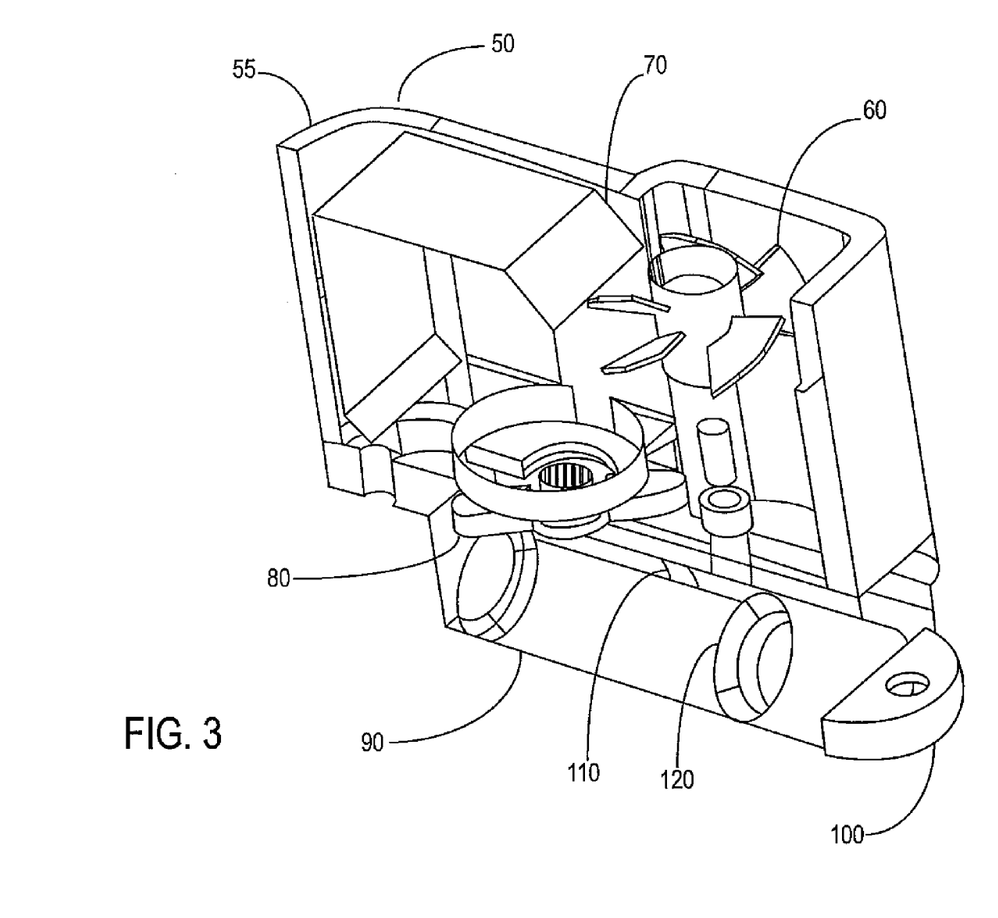
FIG. 3 illustrates a scent cartridge for the scent delivery device according to the present invention.

An embodiment of the scent cartridge is illustrated in FIG. 3. The scent cartridge is referred to generally by numeral 50 and includes a scent reservoir 90 and an electronics housing 55. The housing is fixably connected to the scent reservoir and defines an enclosure with an opening. A valve 80 is connected to the lid of the scent reservoir. A fan 60 is positioned at least partially inside the housing such that, when operating, the fan directs air from within the housing to the outside of the housing, through the opening. A servo 70 controls the position of the valve.

Preferably, the size and weight of the scent cartridge are sufficiently small to allow the cartridge to be comfortably worn by a human adolescent or adult. Preferably, the scent cartridge weighs less than 1.5 lb and has less than 32 inches in dimensions as a whole. Preferably, the size and weight of the scent cartridge are sufficiently small so that a plurality of the cartridges can be attached to a holder and are also wearable.

The scent reservoir 90 has a basin for holding scented materials and includes a lid. The lid is fixably attached to the basin. The lid has one or more openings or scent passages 110 that are sufficiently sized large to permit scent from the scented material to flow from the scent reservoir through the scent passages. Preferably, there are at least two scent passages in the lid.

The lid may be affixed to the basin in any of the usual manners known to those of ordinary skill in the art. In one embodiment of the present invention, the lid is attached to the basin by a set of screws. Alternatively, the basin and the lid may be integral.

The basin and lid are preferably made of lightweight material such as aluminum or Teflon, and may be formed by a mold. The lid and basin may be made of the same or different materials.

A scented material is placed in the scent reservoir 90. The scented material must be produced or formulated such that it can be inhaled by people. It should be non toxic, anti-allergic, non-irritant and as inert as possible in relation to the environment. A large number of possible formulations can be used in the present invention including, but not limited to, formulations containing those scents that emulate common every day odors that are sensed, such as the smell of the rain, wet soil, garden flowers, dust, forests, etc. Such odoriferous substances or compounds can be formulated in the form of releasable solids, liquids or aerosols. The persistence of the scent 3 may be controlled, for instance, through odor inhibiting agents, such as chemical inhibitors.

A scent wick 120 may be placed in the basin for absorbing and releasing a scent. The wick 120 may be made of any suitable absorbent material such as cotton.

The scent reservoir preferably includes a plug 100 at one end of the reservoir for providing slidable and sealable engagement with the electronics housing. The scent reservoir is preferably made of anodized aluminum or other non-reactive metal, or alternately a composite material such as Teflon that does not hold the smell, and provides for a tight sealing engagement with the electronic housing.

Preferably, the size of the basin is large enough to contain sufficient scent material to last through several virtual environment or other sessions lasting 5 to 20 minutes each without refill. In one embodiment, the scent reservoir is 1.90 inches long and 0.6-0.84 inches wide.

Preferably the scent reservoir 90 is refillable. In one embodiment of the present invention, the scent reservoir includes a plug that may be unplugged from the electronics housing 55. A new scent wick 120 is placed in the basin. Alternatively, additional scent may be added into the reservoir through scent passages 110. The unplugged scent reservoir may be thoroughly cleaned before refill using an appropriate neutralizing solution.

The scent cartridge according to the present invention also includes a housing 55 fixably connected to the scent reservoir. The housing 55 is shaped so as to define an enclosure above the scent reservoir and an opening.

The housing 55 may be affixed to the scent reservoir in any of the usual manners known to those of ordinary skill in the art. In one embodiment of the present invention, the housing is attached to scent reservoir by one to several small screws. Alternatively, the basin, the lid and the housing may be integral.

The housing is made of lightweight material such as plastic or metal or other composite lightweight material. In the current embodiment of the device, the housing is formed of machined aluminum, with or without an anodized or clear coating. Alternately the housing may be formed by molding or milling of appropriate materials.

In one embodiment, the overall dimensions of the housing are 1.27 inches×1.9 inches×0.84 inches and the total volume is 2.02 inches$^3$. In another embodiment, the overall dimensions of the housing are 2.4 inches×2.4 inches×0.85 inches and the total volume is 2.02 inches$^3$.

The housing holds a valve 80 fixably connected to the lid of the scent reservoir 90, the valve covering variably a portion of the scent passages. The valve 80, must, in one position, completely cover the scent passages 110 (the "closed" position). Preferably, the valve, in another position does not cover any portion of the scent passages 110 (the "open" position). Most preferably, the valve 80 may be controlled in a manner so that it can partially cover the scent passages 110. The valve is preferably a butterfly valve. The valve is also preferably made of lightweight material such as aluminum, Teflon, Delron impregnated Teflon, or other composite material. Detailed drawings of an exemplary valve can be found at: www.theleeco.com/EFSWEB2.NSF/0/ e3c0d8053c752e9f85256ad10061033d?OpenDocument. In one embodiment of the device, the arm is made of aluminum within an aluminum housing.

A fan 60 is connected to the housing 55 and positioned at least partially inside the housing such that, when operating, the fan directs air from within the housing to the outside of the housing, through the opening. In one embodiment, the fan is upstream of the scent and therefore does not have chemicals passing through it. As the valve rotates, the fresh air flow is reduced, and the scent reservoir inlet and exhaust valve open, allowing the scent to mix into the air flow.

An exemplary fan 60 is a lightweight plastic commercially available 5V DC fan unit manufactured by Sunon: KDE series brushless fan, part number KDE0517PDB2-8. The fan frame size is 17 mm square, made of polybutylene terephthalate (PBT) plastic, with a ball bearing system and variable speed. The frame thickness is 8 mm. The weight of the fan is 4 grams. This fan is available commercially from Sunon Inc., 1075 West Lambert Road, Suite A, Brea, Calif. 92821.

The housing also includes a servo 70, containing means for varying the portion of the scent passages covered by the valve and means for varying the rotation speed of the fan.

Preferably, the server is 20.9 mm long, 11.4 mm wide and 22.0 mm high. The servo weighs 6 grams. An exemplary servo is a Hitec HS-50 Feather Ultra Micro Servo J.

Servo control technology, which is also referred to as "motion control" or "robotics" is used in industrial processes to move a specific load in a controlled fashion. These systems can use either pneumatic, hydraulic, or electromechanical actuation technology. The choice of the actuator type (i.e., the device that provides the energy to move the load) is based on power, speed, precision, and cost requirements. Electromechanical systems are typically used in high precision, low to medium power, and high-speed applications. Motors are the actuators used in electromechanical systems. Through the interaction of electromagnetic fields, they generate power. These motors provide either rotary or linear motion.

In the present invention, the servo is generally a standard three-wire type, where servo control can be achieved via pulse width modulation (PWM). PWM control works by switching the power supplied to the motor on and off very rapidly. The DC voltage is converted to a square-wave signal, alternating between fully on (nearly 12 v) and zero, giving the motor a series of power "kicks". If the switching frequency is high enough, the motor runs at a steady speed due to its fly-wheel momentum. By adjusting the duty cycle of the signal, i.e., the time fraction it is "on," the average power can be varied, and hence the motor speed.

For example, the servo 70 may include a PWM fan control, a PWM valve control, a Fan 0-5V, a speed control circuit, a speed control power, and a servo controller card. Fan 0-5V is plugged into a mating connector on a speed controller. The PWM valve control, fan speed control, and speed control power are plugged into 3 sets of pins on the servo controller card.

Figure 4:
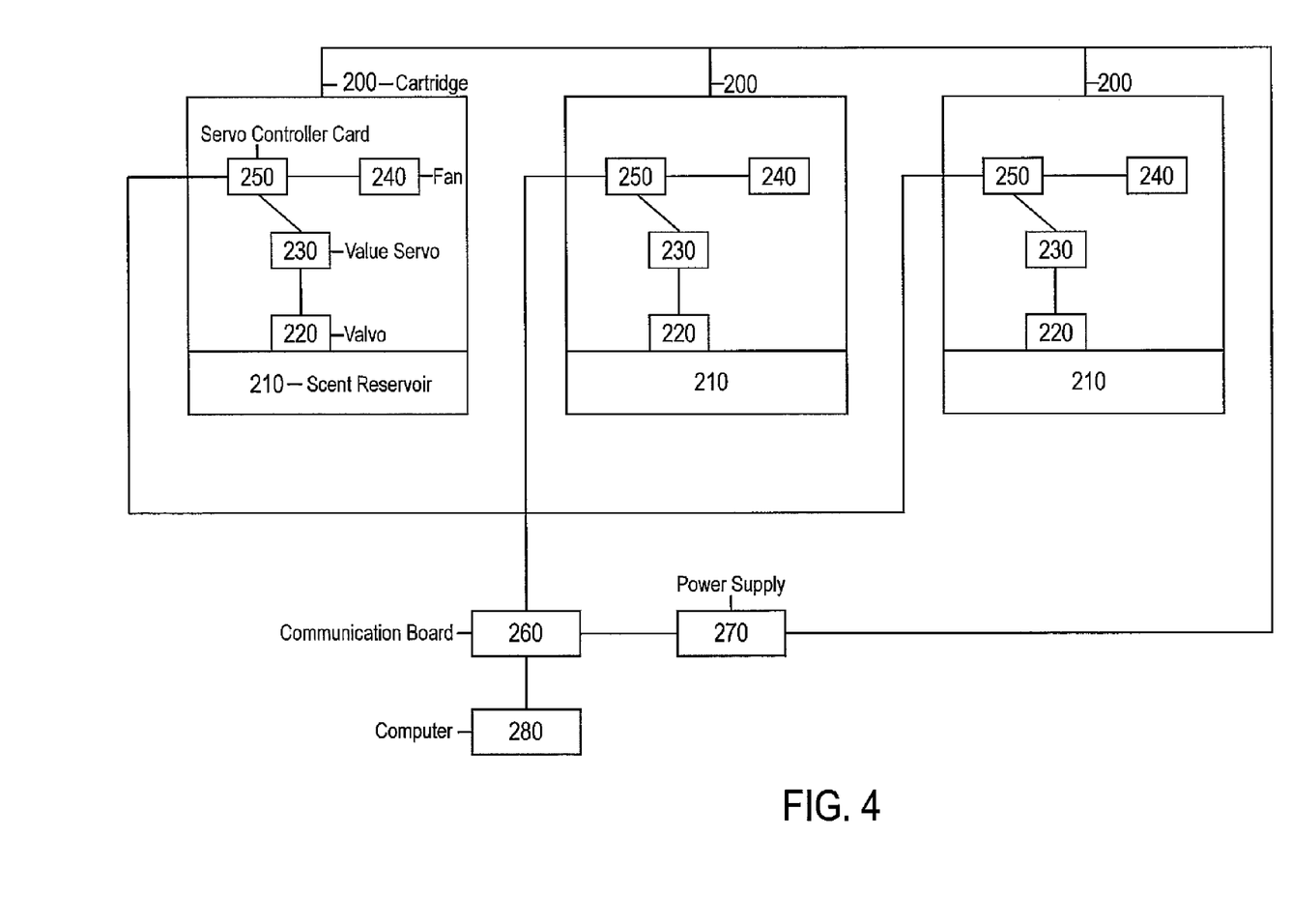
FIG. 4 is a schematic block diagram of a computer controlled scent delivery system constructed according to the invention.

FIG. 4 is a schematic block diagram of a computer controlled scent delivery system constructed according to the invention. The system includes one or more scent cartridges 200, each containing a scent reservoir 210, a valve 220, a valve servo 230, a fan 240, and a servo controller card 250. The servo controller cards are in electrical communication with a communication board 260. Power for the system is provided by a central power supply 270. For example, the power may be symmetrically distributed between pairs of cartridges, sharing power with each pair connected in a series. The communication board is further in electrical communication with a programmable control computer 280.

The computer 280 is programmed for selective releasing of scents from the cartridges 200 in synchronism with visual and/or acoustic representations in a virtual reality environment. The program includes instructions regarding the choice of the scents to be released, the order of the scents to be released, and the amounts of the scents to be released. When a person wearing a scent delivery system of the invention is in a virtual reality environment, the computer sends program instructions in accordance with the visual and/or acoustic representations to the communication board 260. The communication board receives the instructions and relays them to the servo controller cards 250 followed by the valve servos 230 and the fan 240. In each cartridge, the valve servo directs the valve 220 to turn to the programmed position, and the fan 240 spins at the programmed speed. When the valve is at an "open" position, scented air is released from the scent reservoir. The fan directs the air from the inside of the cartridge to the outside, thereby creating olfactory perception of the person in the virtual reality environment. Combined with the visual and/or acoustic representations, the presence of the scent enhances the liveliness of the virtual reality environment.

In operation, the scent reservoir 90 is filled with a scent and plugged into the housing 55 while the valve 80 is set at a "close" position, e.g., the scent passages 110 are completely covered. The valve position is adjusted at small increments to open or partially open the scent passages 110. Scented air flows from the scent reservoir into the electronics housing. The fan speed controller is set to 0 before power is supplied. Once power is supplied, it is ramped up to 255 and then back to 0. This is done each time power is interrupted to the fan. Once complete, the fan speed control is adjusted using values from 0 to 255. Fan 60 usually does not start to spin until about 150. The speed of fan is adjusted to direct the scented air from inside the housing to the outside of the cartridge 50.

The scent delivery system of the invention are particularly useful for releasing scents in a controlled manner. It provides a realistic olfactory experience in a variety of interactive or non-interactive settings such as military training, entertainment, education and medical treatment.

In one embodiment, a wearable scent delivery system is provided for a controlled scent release. The advantage of the wearable scent delivery system is that released odors are localized to the wearer and do not fill up a room, eliminating any mechanism needed to clear the air after each scent release as the minimal amount of scent released will dissipate naturally and quickly from the wearer's immediate surroundings. The wearable system includes one or more scent cartridges, each cartridge containing a different scent. Examples of the scent delivery system and the scent cartridge are shown in FIGS. 2 and 3, respectively. The system also includes an electronic controller triggered mechanically or by a signal from a computer or the environment. Once triggered, the controller processes the signal and instructs the cartridges to release scents in a pre-determined order for pre-determined durations at pre-determined intensities, for example, in accordance with the movements of a participant within a virtual environment.

In another embodiment, the wearable scent delivery system is provided for simulating a virtual reality environment. While a visual and acoustic representation is displayed, the controller receives signals from the representation and responds by instructing the cartridges to release scents consistent with the images and sounds of the representation. Alternatively, a computer is pre-programmed to transmit instructions to the controller during the representation. These instructions direct specific cartridges to release specific amounts of scents at specific times such that the olfactory perception created is in synchronism with the visual and acoustic representation. The wearable scent delivery system (e.g., a collar) allows scents to be delivered to one or more wearers in a highly localized manner with the advantage that the released smells do not linger in the room but dissipate naturally. This arrangement also permits two or more wearers within a virtual environment to each individually experience the smells that are appropriate to any localized portion of the environment.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLE

Scent Cartridge Assembly, Operation, Refill and Cleaning (1) Assembly

Housing Assembly a. Place electronics housing upside down on a flat surface. The paddle valve will be on the top.

b. Place scent vial on top of the electronics housing with the 5 countersunk holes facing up.

c. Insert five 2-56×⅝" screws into the holes and tighten with allen driver provided.

d. Flip device back upright.

Electronics e. Plug "Fan 0-5V" into the mating connector on the speed controller.

f. Plug the PWM Valve Control, the Fan Speed Control, and the Speed Control Power plugs into 3 sets of pins on the servo controller card.

(2) Operation

Setup—Only Needs to be Done Once a. With the two halves of the device unassembled, and the electronics connected to the card, find the servo position value for the vent closed position.

b. Adjust the servo position at small increments to find the vent open position.

Fan Speed Control

The fan speed controller is a must be set to 0 before power is supplied. Once power is supplied, it must be ramped up to 255 and then back to 0. This will need to be done each time power is interrupted to the fan. Once complete, the fan speed control can be adjusted using values from 0-255. The fan will most likely not spin until ~150.

(3) Refill a. With entire housing assembled and the valve in the closed position, remove ⁵⁄₁₆-18×⅜" screw from back of scent vial using allen driver supplied.

b. Insert a wad of cotton or similar wick material to absorb the scent and prevent liquid leakage through open valve during operation.

c. Add scent oil to saturate wick.

d. Replace screw with Teflon O-ring.

(4) Cleaning a. Remove scent vial by unscrewing the 5 screws from the bottom of the device.

b. Remove the fill plug screw shown in the refill instructions.

c. Thoroughly clean scent vial.

While the foregoing has been described in considerable detail and in terms of preferred embodiments, these are not to be construed as limitations on the disclosure or claims to follow. Modifications and changes that are within the purview of those skilled in the art are intended to fall within the scope of the invention. All literatures cited herein are incorporated by reference in their entirety.

What is claimed is:

1. A portable and wearable scent delivery system comprising:

a base adapted for holding at least one or more scent cartridges;

one or more scent cartridges detachably fixed to the base, each one or more scent cartridges having a scent reservoir and a valve, wherein the scent reservoir includes a basin, a scented material placed in the basin, and a lid containing scent passages, and wherein the valve is fixably connected to the lid of the scent reservoir and variably covers a portion of the scent passages;

a communication board detachably fixed to the base, containing a controller and a microprocessor, wherein the microprocessor is capable of receiving input signals from a signal generator through an electronic connection, processing the input signals, and transmitting output signals through the controller to the valve for scent release; and a power supply detachably fixed to the base, providing power to the scent cartridges and the communication board;

wherein said base is in the shape of a collar or necklace and is portable and wearable.

2. The system according to claim 1, wherein the scent cartridge further comprises:

a housing fixably connected to the scent reservoir and defining an enclosure with an opening; and a fan connected to the housing and positioned at least partially inside the housing, wherein the microprocessor is further capable of transmitting output signals through the controller to the fan for directing scented air from within the housing to the outside of the housing through the opening.

3. The system according to claim 1, wherein the electronic connection is a wireless connection.

4. The system according to claim 1, wherein the signal generator is a computer.

5. A method for scent release, comprising:

providing a portable and wearable scent delivery system comprising one or more scent cartridges, each cartridge containing a different scent; and releasing one or more scents from one or more cartridges in a pre-determined order for a pre-determined duration at a pre-determined intensity, in response to a signal received from a computer, wherein the wearable scent delivery system comprises:

a base adapted for holding at least one or more scent cartridges;

one or more scent cartridges detachably fixed to the base, each one or more scent cartridges having a scent reservoir and a valve, wherein the scent reservoir includes a basin, a scented material placed in the basin, and a lid containing scent passages, and wherein the valve is fixably connected to the lid of the scent reservoir and variably covers a portion of the scent passages;

a communication board detachably fixed to the base, containing a controller and a microprocessor, wherein the microprocessor is capable of receiving input signals from a signal generator through an electronic connection, processing the input signals, and transmitting output signals through the controller to the valve for scent release; and a power supply detachably fixed to the base, providing power to the scent cartridges and the communication board;

wherein said base is in the shape of a collar or necklace and is portable and wearable.

6. A method of simulating a virtual reality environment, comprising:

providing a visual and acoustic representation;

providing a portable and wearable scent delivery system comprising one or more scent cartridges, each cartridge containing a different scent; and releasing one or more scents from one or more cartridges in response to a signal received from said environment, wherein the wearable scent delivery system comprises:

a base adapted for holding at least one or more scent cartridges;

one or more scent cartridges detachably fixed to the base, each one or more scent cartridges having a scent reservoir and a valve, wherein the scent reservoir includes a basin, a scented material placed in the basin, and a lid containing scent passages, and wherein the valve is fixably connected to the lid of the scent reservoir and variably covers a portion of the scent passages;

a communication board detachably fixed to the base, containing a controller and a microprocessor, wherein the microprocessor is capable of receiving input signals from a signal generator through an electronic connection, processing the input signals, and transmitting output signals through the controller to the valve for scent release; and a power supply detachably fixed to the base, providing power to the scent cartridges and the communication board;

wherein said base is in the shape of a collar or necklace and is portable and wearable.

* * * * *